United States Patent [19]

Wang

[11] Patent Number: 4,622,207

[45] Date of Patent: Nov. 11, 1986

[54] REAGENT TEST DEVICE HAVING SEALED MATRIX BOUNDARIES

[75] Inventor: Joseph Y. Wang, Elkhart, Ind.

[73] Assignee: Miles Laboratories, Inc., Elkhart, Ind.

[21] Appl. No.: 681,790

[22] Filed: Dec. 14, 1984

[51] Int. Cl.[4] .................. G01N 33/52; G01N 21/78
[52] U.S. Cl. ...................................... 422/56; 427/2; 428/58; 435/805
[58] Field of Search .............. 422/55, 56, 57, 58; 435/805; 427/2; 428/58

[56] References Cited

U.S. PATENT DOCUMENTS

| | | | |
|---|---|---|---|
| 3,001,915 | 9/1961 | Fonner | 422/56 |
| 3,846,247 | 11/1974 | Kronish et al. | 435/38 |
| 4,087,332 | 5/1978 | Hansen | 422/56 |

Primary Examiner—Arnold Turk
Attorney, Agent, or Firm—Roger N. Coe

[57] ABSTRACT

Independent reagent matrix zones are created in hydrophobic open celled natural or synthetic material by heating the open celled material along parallel lines at right angles to the length of a reagent test device so as to seal the material at predetermined intervals and thereby form separate reagent matrix areas on the same reagent test device. This technique results in a reagent test device which eliminates the runover problem which has caused cross contamination between reagent areas and resulted in the failure of reagent test devices to perform properly.

6 Claims, 3 Drawing Figures

REAGENT TEST DEVICE HAVING SEALED MATRIX BOUNDARIES

FIELD OF THE INVENTION

The present invention relates to reagent test devices and, more particularly, reagent test devices which prevent or substantially eliminate runover problems responsible for cross contamination of reagents and interference with determinations or measurements based on colorimetric changes.

BACKGROUND OF THE INVENTION

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so-called "dip-and-read" type reagent test device. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent strip test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constituent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Test devices such as these usually comprise one or more carrier matrices, such as absorbent filter paper, having incorporated therein a particular reagent or reactant system which manifests a detectable response, e.g., a color change, in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855; 3,814,668; etc.

Thus, it is customary for reagent test devices to contain more than one reagent bearing carrier matrix, in which each reagent bearing carrier matrix is capable of detecting a particular constituent in a liquid sample. For example, a reagent test device could contain a reagent bearing carrier matrix responsive to glucose in urine and another matrix responsive to ketones, such as acetoacetate, the ketone responsive matrix being spaced from, but adjacent to, the glucose responsive matrix. Such a product is marketed by Ames Division of Miles Laboratories, Inc. under the trademark KETO-DIASTIX. Another reagent test device marketed by the Ames Division of Miles Laboratories, Inc., N-MULTISTIX, contains eight adjacent reagent incorporated matrices providing analytical measurement of pH, protein, glucose, ketones, bilirubin, occult blood, nitrite, and urobilinogen.

Despite the obvious, time-proven advantages of such multiple reagent test devices misuse can result in misinformation. These multiple analysis tools comprise complex chemical and catalytic systems, each reagent matrix containing an unique reactive system responsive to its particular analyte. Thus, it is possible, if the reagent test device is misused, for chemicals to be transported by the liquid sample being analyzed from one carrier matrix on the reagent test device to another. Should this happen it is possible for reagents from one carrier matrix to interfere with those of another causing unreliable results. Although it is common in the reagent test device industry to provide detailed instructions on how this problem can be avoided, i.e., directions for properly manipulating a reagent test device by blotting excess fluid, etc., nevertheless ignorance or disregard of these instructions can permit reagents from one matrix to run over onto an adjacent one. It is the prevention of this "runover" problem that the present invention is primarily directed.

The elimination of runover has been long sought after and the present discovery, which is the cumulation of an extensive research effort, provides a very effective solution to this problem.

DISCUSSION OF THE PRIOR ART

The patent literature is replete with accounts of myriad attempts at curtailing runover, the great bulk of the emphasis being directed to two basic concepts: the adsorbance of runover liquid by bibulous layers placed beneath the reagent-bearing layers of reagent test devices; and the use of hydrophobic barriers between the spaced matrices. The former has met with moderate success, whereas the latter approach has not.

Of the multilayer type reagent test devices, U.S. Pat. No. 4,160,008 describes a test device in which the carrier matrices containing reagent formulations are provided with adsorbent underlayers which are separated therefrom by sample impervious barrier layers. Each matrix thus forms the upper layer of a laminate composite in which the barrier layer is disposed between the matrix and the adsorbent base layer, the composite being fixed to a suitable support such as a plastic substrate. When the test device is dipped into the liquid sample the portion of sample which would otherwise runover from one matrix to another is largely adsorbed into the underlayer of the latter through the exposed sides, the barrier layer of the composite segregating the adsorbent underlayer from the upper reagent layer.

U.S. Pat. No. 4,301,115 discloses and claims a test device comprising a base support member coated with a hydrophobic barrier layer to which a plurality of spaced apart reagent matrices are affixed. This approach virtually eliminates cross-contamination between adjacent reagent areas of multiple reagent test devices, but requires an extra step of applying hydrophobic material to the base support member of the reagent test device.

With respect to the development and use of barriers and/or barrier materials between reagent matrices, the patent art is replete with teachings, which in theory, at least, would minimize the runover problem. U.S. Pat. No. 3,418,083 discloses an indicator-impregnated adsorbent carrier matrix treated with wax, oil or similar "hydrophobic" agents. It is stated that when a sample of blood is placed on the resulting reagent test device, only colorless liquid components permeate it, the proteinaceous, colored blood components remain on the surface where they can be removed. Thus, it is taught that the liquid portion bearing the analytes permeates the reagent matrix pad and color interference is precluded.

Still another prior art patent, U.S. Pat. No. 3,001,915, describes an adsorbent paper reagent test device having spaced reagent-impregnated test areas for more than one sample component, each such area being separated from the other reagent-impregnated test area by a nonadsorbent barrier portion. The barrier is provided by impregnation with materials such as polystyrene, rosin, paraffin and various cellulose esters. The reagent strip is prepared, according to the reference, by impregnating a portion of a paper pad with a glucose sensitive reagent system. When the reagent strip is dry, a solution of one or more of the barrier materials is applied to the paper adjacent the glucose sensitive reagent material. After further drying a protein sensitive reagent system is applied and the process is repeated with alternate applications of reagent and barrier solutions, with drying steps in between.

Yet an earlier patent, U.S. Pat. No. 2,129,754, describes the impregnation of filter paper with paraffin wax whereby specific areas are left unimpregnated and these areas are treated with indicator systems for a particular analyte.

In U.S. Pat. No. 3,006,735 the concept of barrier material impregnated between reagent areas of a reagent test device is carried one step further by providing successive reagent areas responsive to different degrees of water hardness. Water repellent material, such as oils, waxes, silicones, and printer's varnish, is impregnated between these reagent test areas. Like the preceding two patents this citation is restricted to paper or like bibulous material wherein reagent and barrier material are impregnated sequentially along their length.

Similarly, U.S. Pat. Nos. 3,011,874 and 3,127,281 teach the use of hydrophobic barrier materials impregnated in part of a reagent test device in order to separate one reagent area from another and thereby avoid contamination.

Yet another patent which mentions the separation of indicator reagent sites by the use of nonadsorbent or hydrophobic materials is U.S. Pat. No. 3,964,871.

Whereas the foregoing patents represent what is believed to be the most pertinent prior art to the present invention, it should be noted that currently marketed reagent test device products for the most part contain reagent impregnated matrices affixed to hydrophobic organoplastic material. Thus, the multiple reagent test device known as N-MULTISTIX contains eight different reagent impregnated matrices mounted on polystyrene film. Since polystyrene is hydrophobic, the reagent strip can be said to have hydrophobic interstices between adjacent matrices.

Despite lip service given by prior art accounts to eliminating runover, the fact remains that the problem continues to exist.

Prior art attempts using wax, oils, silicones, etc. have not curtailed runover to a clinically significant extent; and what modest advances have been made are more than offset by serious drawbacks inherent to such attempts. For example, applying hydrophobic material only at reagent area interstices embodies enormous technical problems, especially when compared with the current technique for manufacturing dip-and-read reagent test devices. Besides the obvious extra steps required by interstitial application, there is the danger of some of the hydrophobic material overlapping the reagent area thereby interfering with the paramount purpose of the reagent test device. Moreover, none of the prior art substances provides a suitable surface for adhesion.

Even if the above shortcomings were not prohibitive enough, the prior art hydrophobic substances lack a degree of hydrophobicity required to prevent runover. They do not provide a sufficient contact angle to achieve the required hydrophobicity, nor do they provide a suitable surface for binding either the adsorbent matrices or the reagent, where reagent is coated directly on the substrate surface.

The present invention virtually eliminates cross-contamination between adjacent reagent areas of multiple reagent test device matrices. Success in eliminating runover problems, which causes cross-contamination and results in false determinations, is achieved by employing a different format for reagent strips involving the use of an open-celled, natural or synthetic material which can be heat sealed to close the cell openings at selected positions along the strips to thereby create separate matrices which are effectively isolated from each other.

SUMMARY OF THE INVENTION

An object of the present invention is to replace conventional reagent test devices with a different reagent test device format which prevents or substantially eliminates runover problems between adjoining carrier matrices.

Still another object of the present invention is to provide an inexpensive and effective means for eliminating or materially reducing runover.

In accordance with the present invention, a hydrophobic open celled, natural or synthetic material is heat sealed to close cell openings at selected positions along the test device to thereby create separate matrices which are effectively isolated from each other. By using heat or ultrasonic applications to close cell openings and seal adjacent matrix areas, individual matrices are obtained which are isolated from each other as independent zones. These zones prevent runover problems from occurring between the matrices.

Accordingly, a reagent test device is formed comprising a strip of open celled natural or synthetic material having opposing upper and lower planar, parallel sides and cell openings at spaced locations along the strip of material being sealed to form matrix boundaries thereby defining reagent carrier matrices having parallel surfaces composed of the parallel upper and lower sides of said material, whereby the reagent carrier matrices and the material have the same thickness.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
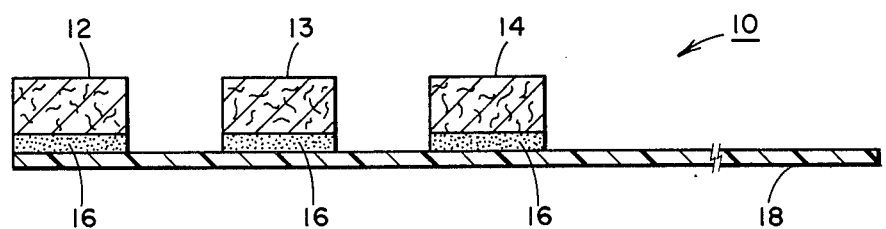
FIG. 1 is a diagramatic side view, in cross-section, illustrating the conventional structure of reagent test devices employing filter paper attached to a substrate.
Figure 2:
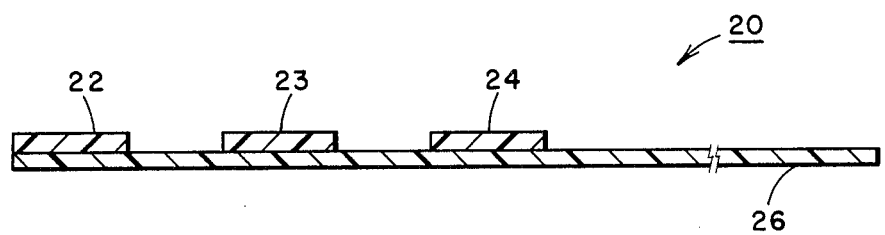
FIG. 2 is a diagramatic side view, in cross-section, illustrating a conventional film strip type test device formed by applying reagent impregnated coating to a substrate.
Figure 3:
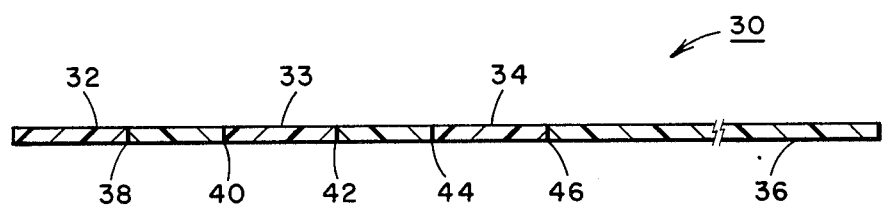
FIG. 3 is a diagramatic side view, in cross-section, illustrating a test device prepared in accordance with the present invention in which the test device is divided into separate zones or matrices by applying heat to close the open cells along boundary lines between individual matrices.

It is believed that the present invention, which is illustrated by FIG. 3 of the drawings, can best be understood by referring to FIGS. 1 and 2 which refer to prior art formats for the formation of reagent test devices.

FIG. 1 presents a typical construction of a reagent test device employing filter paper as the carrier matrix material. Thus, reagent test device 10 in FIG. 1 has absorbent or porous matrix material, 12, 13, and 14, i.e. "carrier matrix", affixed by means of double faced adhesive tape 16 to an insoluble support member, such as organoplastic strip 18. The support member 18 normally has a thickness of about 0.19 mm, a width of about 5 mm and a length which can vary depending on the intended use, the number of reagent matrix areas present, etc. With this construction runover problems can occur even when special precautions are taken or the structure is modified in accordance with the procedures which have been described above.

FIG. 2 illustrates a "film" type reagent test device 20 composed of reagent layers 22, 23 and 24 fixed to suitable substrate 26. Again, as in the case of the reagent test device illustrated in FIG. 1, care must be taken to minimize runover problems between adjacent reagent areas 22 and 23, and 23 and 24, respectively.

FIG. 3 illustrates a reagent test device embodiment 30 in accordance with the present invention. This test device is composed of hydrophobic, open celled material such as polyurethane, polyvinylchloride, cellulose acetate, polystyrene and the like 36 which forms the entire reagent test device. Preferably, for urine testing the pore size of the open cells will be between 0.5 and 100 microns and the thickness of the reagent test device will range between 50 and 1000 microns. For reflection purposes the open celled material 36 is generally white in color or has added pigmentation to make the material white. Individual zones (matrices) are formed by sealing the open cells along lines 38, 40, 42, 44 and 46 to create individual matrices, 32, 33 and 34 in the reagent test device 30. By sealing the cells at certain positions along the reagent test device a reagent test device 30 is constructed such that the separate matrix areas 32, 33 and 34 can be impregnated with the reactive ingredients for each matrix area. These matrix areas remain porous since they have open cells. By heat sealing along lines 38, 40, 42 and 44 and 46 the open cells are destroyed and liquid is not able to flow from one matrix area to another. Thus, when reagent test device 30 is contacted with the material to be tested, either by dipping reagent test device 30 into the sample liquid or by pouring the sample liquid onto reagent matrix area 30, the absorbency of reagent matrix areas 32, 33 and 34 is such as to absorb the liquid to be tested without experiencing the runover problems associated with prior art devices.

Preferably, the material 36 used for formation of reagent test device 30 is strong enough that it can be used as a handle. In other words, the material used should have some inherent strength so that it can be used without requiring lamination of the open celled porous material to a substrate. Nevertheless, the open celled material can be coated, if desired, on a suitable substrate, such as Trycite, or some other inert material.

A preferred manner of sealing the cells along boundary lines 38, 40, 42, 44 and 46 of reagent test device 30 is by the use of high powered ultrasonics to bring about a permanent physical change in the material treated. Thus, by the application of thermal energy or high powered ultrasonics the open celled structure can be modified such that the reagent test device becomes divided into independent zones which are sealed against transfer of liquid from one zone to another. The use of high powered ultrasonics requires a flow of vibratory power per unit of area or volume. The power density is usually operated between 20 and 60 kHz. Any piezoelectric sandwich-type transducer driven by an electronic power source, which is the most common source of ultrasonic power, can be used. One source of suitable ultrasonic equipment is the Branson Sonic Power Company of Danbury, Conn., U.S.A. Ultrasonic heating is fast; usually such heating requires less than a second to create the desired heat seal. Advantageously, such high powered ultrasonic procedures can be automated.

The resultant reagent test device 30 is unique in that the reagent strip with multiple matrices has "0" thickness for the matrix portion, i.e., none extends beyond the surface of the handle. This can be significant in instances where there is a desire to read the reagent test devices instrumentally and it is necessary to avoid damaging the matrix area during the examination. In addition, the structure of the reagent test device in accordance with the present invention is important when one attempts to stack multiple reagent test devices one on top of the other for purposes of automated handling systems. The configuration of the normal reagent test device 10 and even the configuration of the film strip type test device 20 is such that when these reagent test devices are stacked one on the other the bulk of the matrix areas at one end of the reagent test devices is such as to cause the reagent test devices to become skewed. This makes it difficult to properly align the reagent test devices in a cartridge or other holder for purposes of automated handling which facilitates the feeding of one reagent test device at a time from the cartridge or container.

From the foregoing, it will be seen that this invention is well adapted to attain all of the ends and objects hereinabove set forth, together with other advantages which are obvious and which are inherent to the system. The present invention has the advantages of convenience, simplicity, relatively inexpensiveness, positiveness, effectiveness, durability, accuracy and directness of action. The invention substantially overcomes problems associated with runover which have been a continuing and long felt problem with multiple reagent test devices. The invention provides a very effective, simple and inexpensive way of eliminating the runover problem. The test device prepared in accordance with the present invention eliminates the "bridging" of liquid between test matrices on the test device and hence the migration of liquid from one test matrix to another. In addition, the present invention can be conveniently automated to achieve the desired result. Certainly there is no extra layer which must be applied to the reagent test devices in order to control the runover problem.

Obviously, many other modifications and variations of the invention as hereinbefore set forth can be made without the departing from the spirit and scope thereof.

What is claimed is:

1. A reagent test device comprising a strip of hydrophobic open celled natural or synthetic material having opposing upper and lower planar, parallel sides, and cell openings at spaced locations along the strip of material being sealed to form matrix boundaries thereby defining reagent impregnated carrier matrices having parallel surfaces composed of the parallel upper and lower sides of said material, whereby the reagent carrier matrices and the material have the same thickness.

2. The test device of claim 1 in which the open celled material is selected from hydrophobic polyurethane, polyvinyl chloride, cellulose acetate or polystyrene.

3. The test device of claim 1 in which pore size of the open celled material is between 0.5 and 100 microns.

4. The test device of claim 1 in which the thickness of the open celled material is between 50 and 1,000 microns.

5. Process of forming a reagent test device having opposite planar, parallel sides and multiple reagent matrices from a length of hydrophobic open celled natural or synthetic material having a thickness of 50 to 1,000 microns in which the pore size of the open cells is between 0.5 and 100 microns comprising heating the hydrophobic open celled material along lines perpendicular to the length of the test device to close the cells where heat is applied and thereby form matrix boundaries sealing each adjacent reagent matrix area and impregnating said sealed reagent matrices with reactive ingredients, whereby said sealed reagent matrices and the material have the same thickness.

6. The process of claim 5 in which ultrasonics is used to heat the hydrophobic open celled material and seal each matrix area.

* * * * *